United States Patent [19]

Puricelli

[11] Patent Number: 4,559,360

[45] Date of Patent: Dec. 17, 1985

[54] CYSTEINE DERIVATIVES, A PROCESS FOR THEIR PREPARATION, AND PHARMACEUTICAL COMPOSITIONS WHICH CONTAIN THEM

[75] Inventor: Laura Puricelli, Brescia, Italy

[73] Assignee: Magis Farmaceutici S.R.L., Brescia, Italy

[21] Appl. No.: 673,619

[22] Filed: Nov. 21, 1984

[30] Foreign Application Priority Data

Nov. 23, 1984 [IT] Italy ............................... 23844 A/83

[51] Int. Cl.$^4$ ................. A61K 31/165; A61K 31/245; C07C 103/50; C07C 69/157
[52] U.S. Cl. ................................... 514/548; 260/546; 514/562; 560/142
[58] Field of Search ................ 260/546; 514/539, 550, 514/562, 548; 560/142; 562/557

[56] References Cited

U.S. PATENT DOCUMENTS

| | | | |
|---|---|---|---|
| 3,591,686 | 7/1971 | Sheffner | 514/550 |
| 3,981,910 | 9/1976 | Offermanns et al. | 560/142 |
| 4,093,740 | 6/1978 | Fahneustich et al. | 514/562 |

Primary Examiner—Natalie Trousof
Assistant Examiner—John T. Sullivan
Attorney, Agent, or Firm—Stevens, Davis, Miller & Mosher

[57] ABSTRACT

New cysteine derivatives of mucolytic, antipyretic, analgesic and anti-inflammatory action are described, which are obtained by condensing S-(carboxymethyl)-L-cysteine with acetylsalicylic acid. The present invention also relates to salts of the new compounds formed with alkaline and/or alkaline-earth metals, ammonium salts, salts formed with compatible amines, with amino acids or with physiologically acceptable acids. A process is also described for their preparation.

8 Claims, No Drawings

CYSTEINE DERIVATIVES, A PROCESS FOR THEIR PREPARATION, AND PHARMACEUTICAL COMPOSITIONS WHICH CONTAIN THEM

Acetylsalicylic acid is a compound which has been known for some time, and possesses considerable antipyretic, analgesic and anti-inflammatory activity. S-(carboxymethyl)-L-cysteine is also a known product. It is used in the treatment of respiratory infections because of its marked mucolytic action.

It has been found that by combining S-(carboxymethyl)-L-cysteine with acetylsalicylic acid, new derivatives are obtained possessing marked antipyretic, analgesic, mucolytic and anti-inflammatory activity.

Thus the new derivatives combine the properties of the two drugs from which they derive, but do not exhibit a proportional increase in toxicity.

The present invention therefore relates to the new compounds corresponding to the general formula:

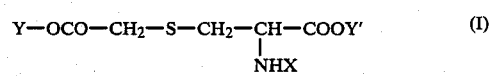

wherein Y, Y' and X are the same or different and can be either H or the acetylsalicylic group, with at least one of the member being the acetylsalicylic group. The invention comprises also the physiologiacally acceptable salts of the above compounds. Such salts in the case of compounds of formula (I) wherein Y and/or Y' are H, and X is the acetylsalicylic group, are the salts formed with alkaline or alkaline-earth metals, whereas in the case of compounds of formula (I) wherein X is H, the salts are formed with physiologically acceptable acids.

The first category includes the salts of (I) with elements such as, inter alia, sodium, potassium, calcium and magnesium, the ammonium salt, the salts with non-toxic amines such as trialkylamine, procaine, dibenzylamine, betaine, choline, carnitine, and the salts with amino acids such as arginine, lysine, methionine, ornithine and proline.

The second category includes the salts of (I) formed with physiologically acceptable organic and inorganic acids such as hydrochloric acid, sulphuric acid, hydrobromic acid, hydroiodic acid, phosphoric acid, nitric acid, malonic acid, succinic acid, maleic acid, citric acid etc.

In addition to their excellent pharmacological properties as stated above, the new derivatives and their salts are characterised by very low toxicity, excellent local tolerability, an absence of side effects on the cardio-vascular system, and low ulcerogenic activity compared with equivalent quantities of acetylsalicylic acid. The present invention also relates to a process for preparing the new derivatives of formula (I), which consists of reacting S-(carboxymethyl)-L-cysteine, or one of its salts, with the chloride of acetylsalicylic acid, in the presence of solvents, while maintaining the temperature between 0° C. and 30° C.

Suitable solvents are benzene, tetrahydrofuran and ether. In the case of compounds of formula (I) wherein X is acetylsalicylic, the solution is kept constantly at an alkaline pH by adding sodium hydroxide solution. An acid acceptor such as triethtylamine can also be used.

The preparation of a compound of this type can be represented by the following scheme:

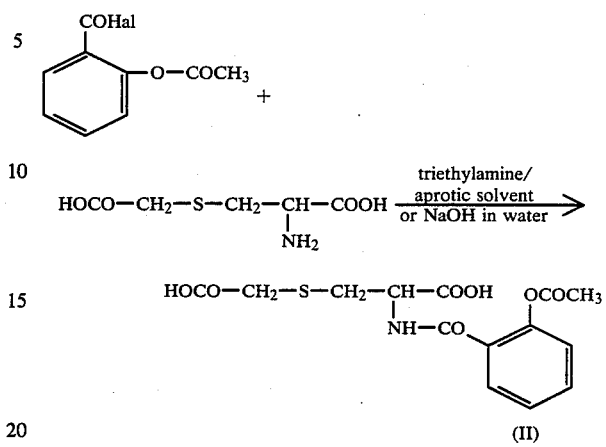

where Hal represents a halogen atom.

On termination of the reaction, the acquired product is isolated, for example by filtration, dried and crystallized.

The process for preparing salt of the compound of formula (II) includes precipitation in organic solvents, lyophilization of their solutions, or the extemporaneous formation of equimolar quantities with sodium carbonate or potassium carbonate.

The preparation of compounds of formula (I) wherein Y and/or Y' are acetylsalicylic groups can be represented as follows:

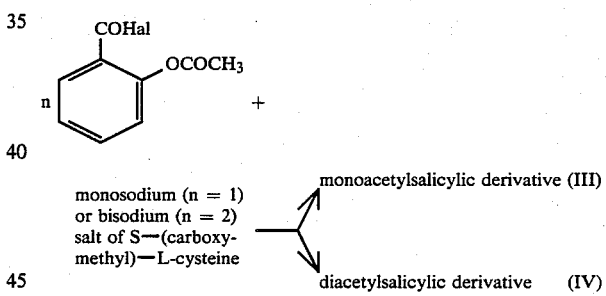

To prepare salts of the derivatives (III) or (IV), their aqueous solution are lyophilized, or their solutions in isopropyl alcohol are treated with an equivalent quantity of the desired anhydrous acid, and the salts separate as precipitate.

The compounds of formula (III) and (IV) can also be isolated by filtration and then purified in the usual manner.

The new compounds of formula (I) exert marked mucolytic, antipyretic, analgesic and anti-inflammatory action. A further subject matter of the present invention are therefore pharmaceutical composition containing a therapeutically active quantity of active principle dissolved in and/or mixed with a suitable liquid or solid support normally used for such compositions.

The active principles can be administered orally, rectally, topically, as an aerosol, or can be injected by intramuscular or intravenous injection.

For oral, rectal or topical administration, a non-toxic pharmaceutical preparation can be formed by mixing the active substance with supports normally used for this purpose, for example starch, glucose, lactose, gelatin, magnesium stearate, glycerin monostearate, talc, sodium chloride, propylene glycol, ethanol etc.

The final products are in the form of capsules, tablets, pills, single-dose sachets, extemporaneous suspensions or extemporaneous emulsions.

For rectal administration, the active substance is mixed with the normal semi-synthetic glycerides, whereas for aerosol administration the active substance can be mixed with the conventional fluorinated propellants.

With regard to these supports, diluents, emulsifiers etc., reference can be made for example to L. G. Goodman, A. Gilman, The Pharmacological Basis of Therapeutics.

In the treatment of catarrhal affections of the respiratory passages, and as adjuvants in treating respiratory phlogosis complications of the common cold and influenza, the compounds of the invention can be administered in quantities varying from 5 to 20 mg/kg per day divided into a number of doses throughout the day, such as three or four times a day.

The pharmaceutical formulations of the invention can be administered in physiological units containing for example 65, 125, 250, 500, 750 and 1000 mg of active principle, together with physiologically suitable supports and excipients.

It has been found that the compounds of the invention exert mucolytic, antipyretic, antirheumatic and analgesic activities which are extraoridinarily marked, while at the same time presenting excellent stability and excellent absorption when administered in the various aforesaid pharmaceutical forms.

The examples given hereinafter illustrate the invention but are not meant to limit the invention in any way. The structure of the described compounds was confirmed by analytical data and spectroscopic examination.

EXAMPLE 1

Preparation of S-(carboxymethyl)-N-(2-acetoxybenzoyl)-L-cysteine MSF 001

80 ml of anhydrous tetrahydrofuran are fed into a 200 ml flask fitted with an agitator and separating funnel, and 17.91 g of S-(carboxymethyl)-L-cysteine and 20.2 g of triethylamine are added under agitation.

When dissolution is complete, 19.86 g of 2-(acetoxy)-benzoyl chloride are added under agitation, while maintaining the temperature at 25°–28° C.

The mixture is maintained at 25°–28° C. under agitation for one hour, it is filtered, and then evaporated to low volume under vacuum. The residue is taken up in 100 ml of water and the pH is adjusted to 5.0 with concentrated hydrochloric acid. The precipitate which forms is dried in an oven. About 25 g of product is obtained, of 99% purity.

Single stain on chromatography. Impurities present: acetylsalicylic acid 0.5%; salicylic acid 0.5%; S-(carboxymethyl)-N-(2-hydroxybenzol)-L-cysteine 1%.

| Elementary analysis | C | H | N | S |
|---|---|---|---|---|
| calculated | 49.26 | 4.4 | 4.10 | 9.4 |
| found | 49.3 | 4.35 | 4.15 | 9.3 |

M.W. 341

EXAMPLE 2

Preparation of S-(carboxymethyl)-N-(2-acetoxybenzoyl)-L-cysteine MFS 001

A solution of 17.91 g (0.1 moles) of S-(carboxymethyl)-L-cysteine in 75 ml of 2N sodium hydroxide is fed into a 200 ml flask fitted with a mechanical agitator and two separating funnels. The solution is cooled to about 5° C., after which 19.86 g of 2(acetoxy)-benzoyl chloride dissolved in 20 ml of benzene, and 25 ml of a 4N sodium hydroxide solution are added over a period of 20–25 minutes under agitation, while maintaining the mixture continuously at 5° C.

The mixture is agitated for a further 10 minutes. The benzene phase is separated, and the acqueous solution is adjusted to pH 5 with hydrochloric acid. The precipitate which forms is dried in an oven. About 26 g of product is obtained, having analytical characteristics equal to those of the product obtained in Example 1.

EXAMPLE 3

Preparation of S-(carboxymethyl)-L-cysteine acetylsalicylanhydride MSF 002 20.1 g of the monosodium salt of anhydrous S-(carboxymethyl)-L cysteine are fed into a flask fitted with an agitator, reflux condenser and separating funnel. While maintaining the temperature at 25° C., 19.86 g of 2-(acetoxy)-benzoyl chloride in 10 ml of ether are added slowly. When the addition is complete, the product is extracted with 100 ml of ethyl acetate, filtered and evaporated to dryness under vacuum. About 31 g of product is obtained.

| Elementary analysis | C | H | N | S |
|---|---|---|---|---|
| calculated | 49.26 | 4.4 | 4.10 | 9.4 |
| found | 49.25 | 4.4 | 4.14 | 9.35 |

M.W.: 341

EXAMPLE 4

Preparation of S-carboxymethylcysteine bis-acetylsalicylanhydride MSF 003

22.3 g of bisodium salt of anhydrous S-(carboxymethyl)-L-cysteine are fed into a flask fitted with an agitator, reflux condenser and separating funnel. While maintaining the temperature at 25° C., 39.72 g of 2-(acetoxy)-benzoyl chloride in 20 ml of ether is added slowly. When the addition is complete, the product is extracted with 150 ml of ethyl acetate, filtered and evaporated to dryness under vacuum. About 40 g of product is obtained.

| Elementary analysis | C | H | N | S |
|---|---|---|---|---|
| calculated | 54.87 | 4.17 | 2.78 | 6.36 |
| found | 54.85 | 4.10 | 2.8 | 6.4 |

M.W.: 503

EXAMPLE 5

Preparation of S-(carboxymethyl)-N-(2-acetoxybenzoyl)-L-cysteine, bisodium salt 22.1 g of 2-(carboxymethyl)-N-(2-acetoxybenzoyl)-L-cysteine are suspended in 50 ml of water. While maintaining the temperature at 5° C., a 40% NaOH solution is added until dissolution is complete, the resultant solution is filtered and the filtrate is lyophilized.

EXAMPLE 6

Preparation of
S-(carboxymethyl)-N-(2-acetoxybenzoyl)-L-cysteine,
lysine salt 22.1 g of S-(carboxymethyl)-N-(2-acetoxybenzoyl)-L-cysteine are suspended under agitation in 100 ml of isopropyl alcohol. 60 g of 50% lysine solution are added under agitation. Agitation is continued until complete dissolution is attained, when 400 ml of ethyl ether is added, again under agitation. The precipitate which forms is filtered off, washed with ether and dried in an oven. About 40 g of product is obtained.

EXAMPLE 7

Preparation of S-carboxymethylcysteine hydrochloride acetylsalicyl anhydride.

22 g of the compound of Example 3 is suspended in water. Dissolution is effected with concentrated hydrochloric acid under agitation, the solution is filtered and the filtrate lyophilised.

EXAMPLE 8

Preparation of S-carboxymethylcysteine hydrochloride bis-acetyl-salicyl anhydride 24 g of the compound of Example 4 are dissolved in 200 ml of isopropyl alcohol, and hydrochloric acid gas is added. A precipitate forms, which is filtered off, washed with ether and dried in an oven. The pharmacobiological characteristics of the new compounds according to the present invention, i.e., their high activity and practical absence of side effects, were evaluated with particular reference to acute toxicity, tolerability, and anti-inflammatory, antipyretic and anti-bronchial activity. Pharmacokinetic tests were also carried out.

ACUTE TOXICITY

The acute toxicity of the proucts was studied on male and female adult mice of Swiss stock, and on male and female adult rats of Sprague-Dawley stock, by oral and subcutaneous administration. For each method of administration, the tested doses were administered in geometrical progression to 10 animals (5 males and 5 females). After treatment, the animals were kept under observation for 7 days. On termination of this period, the $LD_{50}$ and the relative confidence limits were calculated by the Litchfield and Wilcoxon method (Pharmacol. Exp. Ther. 96–99, 1949).

The $LD_{50}$ values are given in Table 1.

TABLE 1

| Animal | Method of administration | PRODUCT MSF 01 | MSF 02 | MSF 03 |
|---|---|---|---|---|
| Rat | oral | 4800 mg/kg | 4800 mg/kg | 4500 mg/kg |
|  | subcutaneous | 4500 mg/kg | 4500 mg/kg | 4200 mg/kg |
| Mouse | oral | 4800 mg/kg | 4600 mg/kg | 4300 mg/kg |
|  | subcutaneous | 4500 mg/kg | 4400 mg/kg | 4100 mg/kg |

TOLERABILITY TESTS

Action on the cardio-vascular system

The test was carried out on 10 male rabbits of New Zealand stock, anesthetised with ethylurethane in doses of 2 mg/kg intraperitoneally, and immobilised with 800 mg doses of each of the new compounds by rectal administration and 800 mg doses of each of the new compounds by endoduodenal administration.

None of the new compounds resulted in modification of arterial pressure, respiration amplitude and frequency, or electrocardiographic trace.

Local tolerability

The test was carried out on 8 native rabbits (4 males and 4 females) for each product.

The animals were treated with the new compounds daily over a period of two weeks, by aerosol administration using a special mask, at doses of 500 mg/kg.

On termination of the treatment the animals were sacrificed. The mucous membrane of the oral cavity was observed with a magnifying lens, and histological preparations were made up from the same zone. Neither the macroscopic not the microscopic observation showed any alteration which could be imputed to the treatment.

Anti-inflammatory activity in the rat

The anti-inflammatory activity of the new compounds was studied in rats by following the experimental method of inducing edema by carrageen. For this purpose, female rats of Sprague-Dawley stock having a weight of 160–180 mg were used, diveded into batches of 10 animals each and treated with doses of 400 mg/kg orally and 400 mg/kg rectally, and compared with 220 mg/kg doses of aspirin.

The oral and rectal treatment with 400 mg/kg of the new compounds significantly reduced edema induced by carrageen.

The activity of the new compounds coincides quantitatively with that of equimolar doses of aspirin.

Antipyrectic activity in the rabbit

The test was carried out on 20 male rabbits of New Zealand stock divided into 4 groups of animals.

Hyperthermia was induced in all the animals by administering 1 ml of polyvalent antipyogenic vaccine into the marginal vein of the ear.

After 8 hours, each group of animals orally or rectally received 400 mg/kg doses of the new compounds and 200 mg/kg doses of aspirin. The body temperature was taken 1, 8, 10, 12 and 14 hours after administration.

The new compounds showed antipyretic activity which coincided quantitatively with that of equimolar doses of aspirin.

ANTIBRONCHIAL ACTIVITY

Experimental bronchitis in the rat induced by $SO_2$ inhalation

The mucolytic activity of the new compounds was determined by producing a bronchial suffering in male Sprague-Dawley rats of body weight 300–350 mg by $SO_2$ inhalation.

The animals were divided into three groups:
Group I: this received only the intoxicating treatment ($SO_2$)
Group II: this received $SO_2$ intoxication and was treated orally with the new compounds in doses of 50 mg/kg
Group III: this received $SO_2$ intoxication and was treated by aerosol with the new compounds in doses of 50 mg/kg.

After intoxication extending over 15 days, by subjecting the rats to 2 hours of $SO_2$ inhalation per day for periods of 15 days, the animals were sacrificed.

Macroscopic examinations were made of the lungs and trachea, with visualisation of the broncho-pulmonary alterations by colouring with Schiff reagent, this being specific for showing up mucopolysaccharides.

From the results obtained and the relative statistical analysis, it was found that the new compounds possess considerable protective action against experimental bronchitis induced in the rat by $SO_2$ aerosol.

The new compounds proved equally active, whether administered orally, by aerosol, by intramuscular injection or by intravenous injection.

Experimental bronchitis induced by citric acid in the guinea pig

Experimental bronchitis was induced by citric acid inhalation, and the tests described in the preceding paragraph were carried out.

Again, the new compounds showed protective action when administered orally, by aerosol, by intramuscular or intravenous injection, or rectally.

Pharmacokinetics

This test was carried out on 10 male rabbits of New Zealand stock, having an average weight of 3.4 kg, they were treated orally and rectally with the new derivatives at a dose of 500 mg/kg.

A salicemia study showed that maximum levels in the serum are attained six hours after treatment, independently of the manner in which the new compounds are administered, and levels are reduced slowly until they disappear within 48 hours.

I claim:

1. S-(carboxymethyl)-L-cysteine compound of the formula:

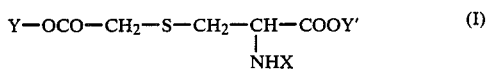

wherein Y, Y' and X are the same or different, and are either H or acetylsalicylic and at least one of Y, Y' and X is acetylsalicylic.

2. The S-(carboxymethyl)-L-cysteine compound according to claim 1, wherein Y and Y' are H, and X is acetylsalicylic.

3. The S-(carboxymethyl)-L-cysteine compound according to claim 1, wherein Y is acetylsalilcylic and Y', and X are H.

4. The S-(carboxymethyl)-L-cysteine compound according to claim 1, wherein Y' is acetylsalicylic and Y, and X are H.

5. The S-(carboxymethyl)-L-cysteine compound according to claim 1, wherein Y and Y' are acetylsalicylic and X is H.

6. Alkaline or alkaline-earth or a non-toxic amine salt of the compound of claim 1, wherein at least one of Y, and Y' is H.

7. Therapeutically acceptable inorganic or organic salts of the compound of formula (I) as defined in claim 1 wherein X is H.

8. A pharmaceutical composition comprising: a mucolytically, an anti-inflammatorally, or an analgesically effective amount of the compound of formula (I) as defined in claim 1, or pharmaceutically acceptable salts thereof and a pharmaceutically acceptable carrier.

* * * * *